United States Patent [19]

Ward, Jr. et al.

[11] 4,409,172
[45] Oct. 11, 1983

[54] DEVICE AND METHOD FOR FABRICATING MULTI-LAYER TUBING USING A FREELY SUSPENDED MANDREL

[75] Inventors: Robert S. Ward, Jr., Lafayette; Donald R. Beckham, Livermore, both of Calif.

[73] Assignee: Thoratec Laboratories Corporation, Berkeley, Calif.

[21] Appl. No.: 234,120

[22] Filed: Feb. 13, 1981

[51] Int. Cl.³ .............................. B29F 3/00; B29C 1/00
[52] U.S. Cl. ................................ 264/209.2; 118/404; 118/405; 264/209.8; 264/213; 264/255; 264/323; 425/113; 425/446; 425/457; 425/467
[58] Field of Search ................. 264/255, 209.1, 209.2, 264/165, 176 R, 301, 303, 304, 305, 308, 299, 310, 323, 212, 173, 213, 209.8, 323; 164/94, 95, 421, 422, 419, 461, 465; 425/803, 224, 90, 376 B, 378 R, 380, 92, 97, 113, 114, 467, 381, 224, 457, 445, 446; 118/404, 405

[56] References Cited

U.S. PATENT DOCUMENTS

| 204,227 | 5/1978 | Hyatt | 264/174 |
|---|---|---|---|
| 223,077 | 12/1879 | Tasker | 164/421 |
| 285,673 | 9/1883 | Phillips | 118/405 |
| 2,533,986 | 12/1950 | Atterbury | 264/299 |
| 2,602,980 | 7/1952 | Bryan | 118/404 |
| 2,616,126 | 11/1952 | Merck et al. | 425/97 |
| 2,778,404 | 1/1957 | Macy et al. | 118/405 |
| 3,212,154 | 10/1965 | Crumpler | 264/176 R |
| 3,233,582 | 2/1966 | Sharetts et al. | 118/404 |
| 3,409,068 | 11/1968 | Yearley et al. | 164/421 |
| 4,022,933 | 5/1977 | Lee | 118/404 |

FOREIGN PATENT DOCUMENTS

| 115378 | 6/1941 | Australia | 118/404 |
|---|---|---|---|
| 1117021 | 6/1968 | United Kingdom . | |
| 1389738 | 4/1975 | United Kingdom . | |

Primary Examiner—Willard E. Hoag
Attorney, Agent, or Firm—Flehr, Hohbach, Test, Albritton & Herbert

[57] ABSTRACT

A device for fabricating multi-layer tubing has a reservoir for tubing solution and discharges such solution from an opening in the reservoir bottom. The reservoir is suspended so as to remain level. Extending through the opening is a vertical rod of smaller diameter but itself suspended by a flexible wire so as to remain vertical. Material in the reservoir extrudes as an annulus even in cross-section by passing between the edge of the reservoir opening and the rod. Such extruded material hardens into one layer of the tubing. There is a repetition with a larger reservoir opening and so depositing a larger tube that is dried on and over the first tube. This is repeated as often as desired to get a finished tube of the proper inside and outside diameter.

The method is following in succession the steps described above.

18 Claims, 5 Drawing Figures

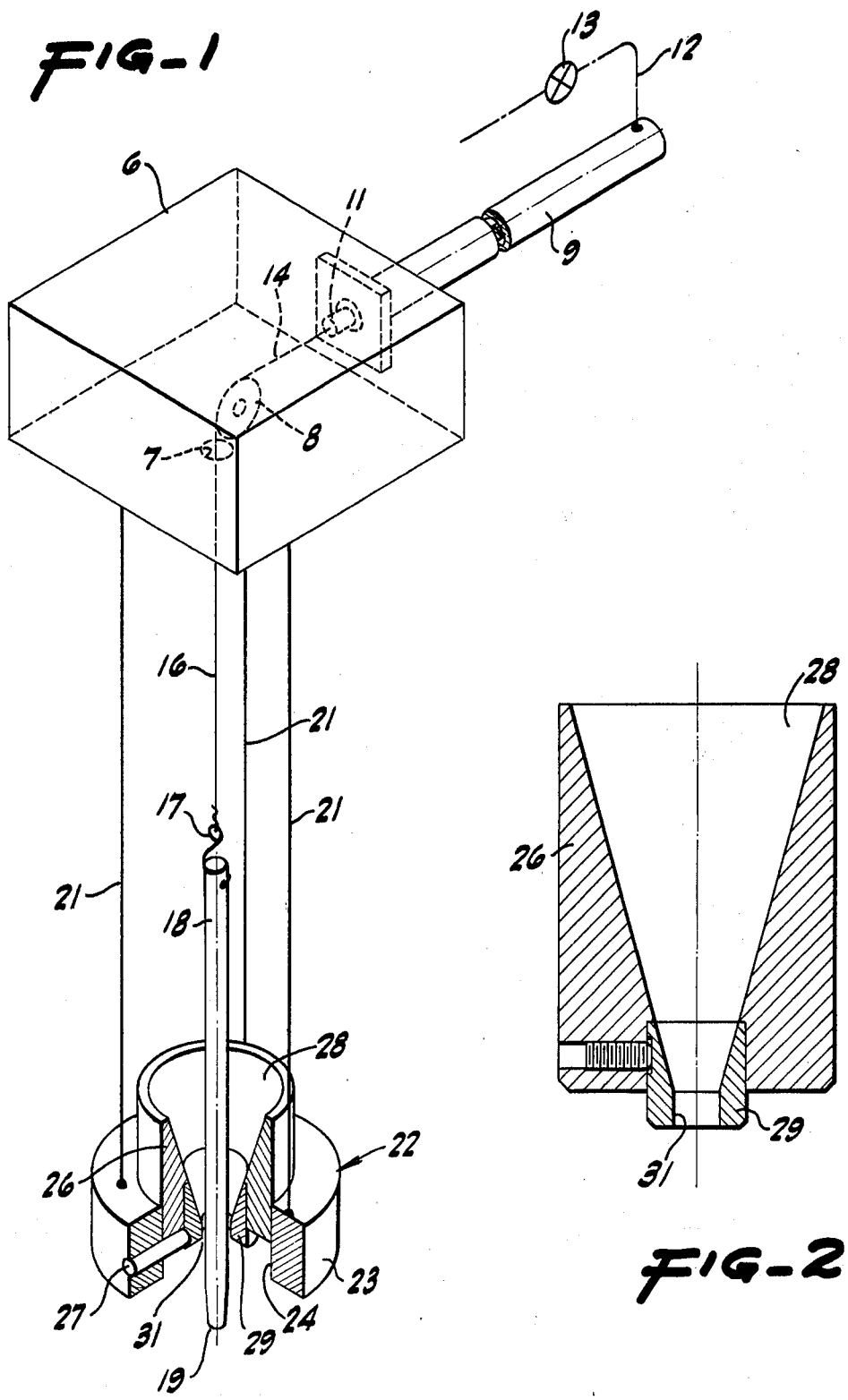

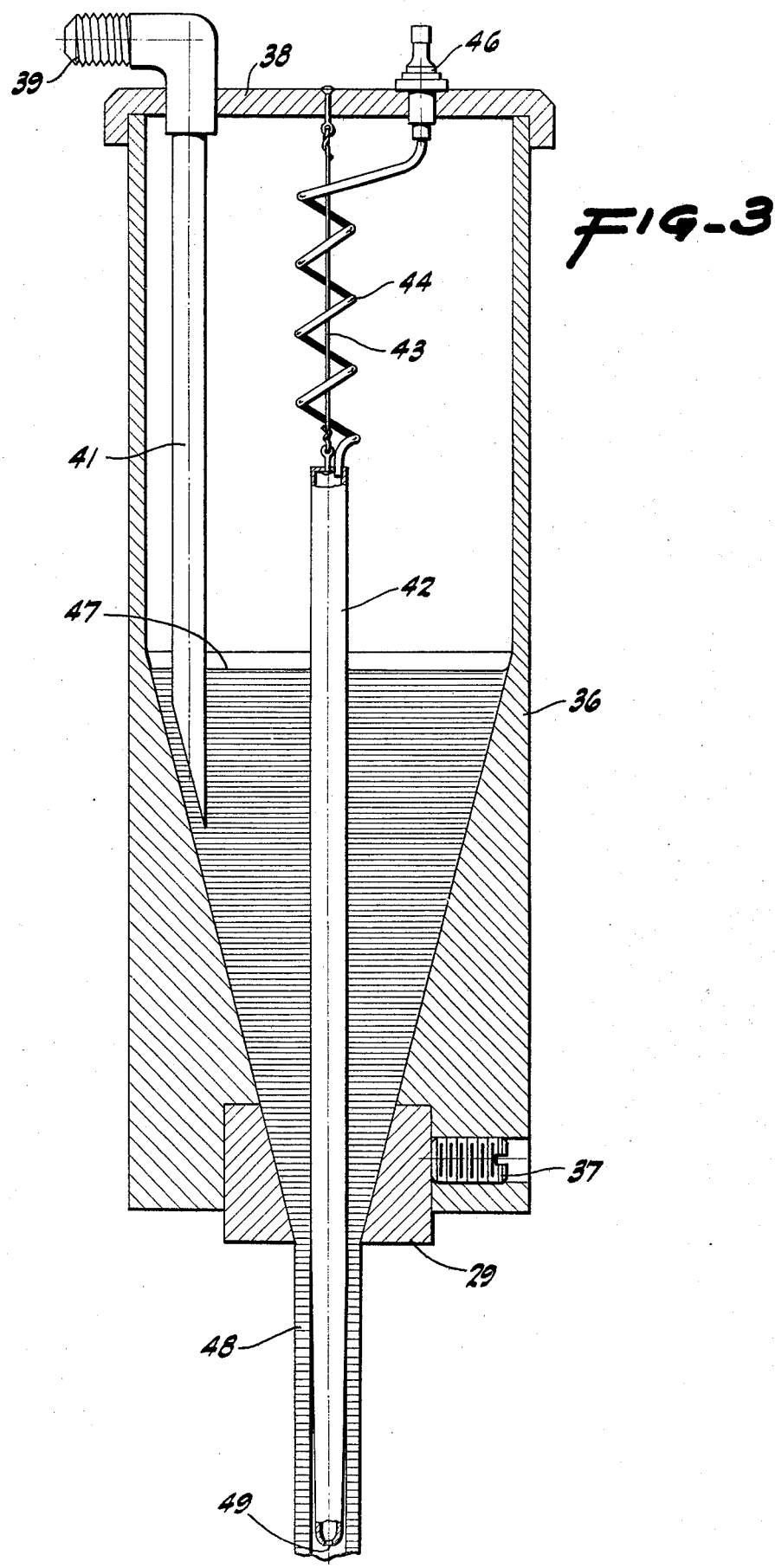

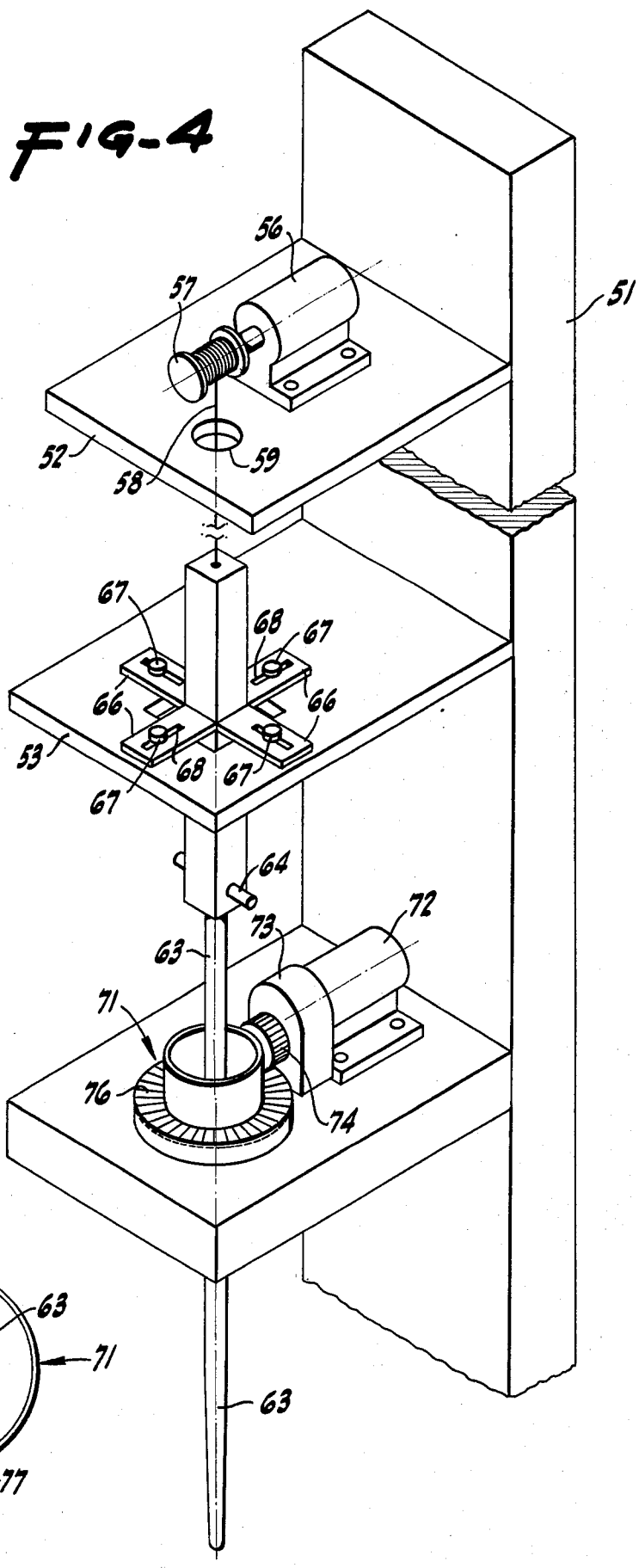

DEVICE AND METHOD FOR FABRICATING MULTI-LAYER TUBING USING A FREELY SUSPENDED MANDREL

BRIEF SUMMARY OF THE INVENTION

A device for fabricating multi-layer tubing has a reservoir for tubing solution, the reservoir having an opening in the bottom thereof for receiving a removable die. The reservoir is carried by a support and a freely suspended, selfcentering mandrel can be moved vertically through the die opening being employed. Alternatively, the mandrel can be vertically stationary.

A method for fabricating multi-layer tubing includes vertically passing a freely suspended rod through a die opening in the bottom of a reservoir containing tubing solution. Preferably the operation is done successively through openings of increasing size. Finally the resulting solidified layers of tubing material are stripped from the rod.

BRIEF DESCRIPTION OF THE SEVERAL VIEWS OF THE DRAWING

FIG. 1 is a diagrammatic perspective showing a form of device for use in fabricating the multi-layer tubing, certain portions being broken away.

FIG. 2 is a cross-section on a vertical axial plane through the die and reservoir portion of the structure shown in FIG. 1.

FIG. 3 is a cross-section on a central vertical plane through a modified form of reservoir, die and mandrel arrangement with the mandrel being vertically stationary with respect to the die.

FIG. 4 is a diagrammatic perspective showing another alternative form of the device wherein there is relative rotation between the mandrel and the die.

FIG. 5 is a cross sectional view of a die and mandrel used in the device of FIG. 4.

DETAILED DESCRIPTION

It is often desired to make a flexible tubing or to make tubular articles having a number of superposed, tightly adhering layers or zones. Particularly desired are articles that can be utilized in prosthetic environments in the human body and comparable zones. It is usually desired to have such tubing of relatively light, flexible character and quite impermeable at least to certain components of the fluids which it normally encounters. It is also frequently desired to have such tubing with an entirely compatible exterior surface and particularly with a quite smooth and compatible interior surface, especially when such tubing is utilized as a substitute for a blood vessel, either venous or arterial.

According to the present arrangement, there is provided in any suitable environment (ordinary supporting structures and the like being omitted for clarity) a basic support platform 6 having a central aperture 7 adjacent which is mounted a pulley 8. Alongside the pulley and fastened to the base 6 is an operating cylinder 9 and piston 11 reciprocable therein. These are under control of an operating fluid in a pipe 12 having a regulating valve 13 therein. The piston 11 is connected to a cord 14 which passes over the pulley 8 and extends through the aperture 7 and has a depending section 16 hanging freely by gravity.

To the lower end of the cord 16 there is attached a connecting device 17 in engagement with a freely hanging mandrel 18. This conveniently is a rod or rod-like member, often having a somewhat slimmed and tapered lower end 19, but generally being circular cylindrical in configuration throughout most of its length.

Also mounted on the platform 6, preferably by three equidistantly spaced, flexible hanging members 21 is a die assembly 22. The hanging members 21 are also equally spaced on the die assembly 22.

The die assembly 22 preferably includes a ring or annulus shaped base 23 having a central bore 24 into which a reservoir 26 is inserted in a removable fashion. The reservoir is normally sustained in position on pins 27 or a shoulder of matching configuration on the base 23. The reservoir 26 is removably positioned about the same axis as the die assembly 22. The reservoir 26 has a conical interior 28 open at the top and tapering downwardly. The reservoir receives and its interior wall 28 is continued by a die 29 adapted to be retained within the reservoir. The die has a central opening 31 in the bottom thereof which is of a particular, accurate diameter. This diameter is a predetermined amount larger than the diameter of the mandrel 18, so that the mandrel or rod can pass freely in a vertical axial direction through the opening 31.

The arrangement is such that the die assembly itself is freely suspended and without any substantial lateral constraint, being therefore free automatically to assume any appropriate, generally vertical axis. Similarly, the mandrel is freely suspended without any substantial lateral restraint and can likewise maintain a generally vertical axis. The arrangement is such that the axis of the opening 31 and the axis of the mandrel are preferably always substantially coincident. During the formation of the tubing the space between the mandrel 18 and the die 29 is always, because of the free suspensions, a substantially true annulus having a predetermined diameter both interiorly and exteriorly. The wall thickness of the resultant tubing will, therefore, be uniform.

In the operation of this structure, it is first arranged that the mandrel be positioned substantially as shown in FIG. 1 with its lower, sometimes tapered, end just barely projecting through the opening 31 and arranged below the bottom portion of the die 29. Into the cylindrical or conical reservoir 36 and within the annular space about the mandrel 18 there is placed a mass of tubing solution. This material varies from time to time, depending upon the nature of the tubing being produced, and is sufficiently well known so that it is not specified in any of its numerous details herein. The tubing material is, however, substantially of a free-flowing liquid nature initially, but has the ability to cure and be solidified such for instance, as in air by the passage of time; by heat; by extraction in a fluid; or by chemical reaction.

With the initial arrangement as described; that is, with the rod depending slightly through the reservoir and surrounded by appropriate tubing solution, the valve 13 is manipulated so that the actuator 9 expels its piston 11 and so moves the line runs 14 and 16 so that the mandrel 18 is gradually lowered through the reservoir and particularly through the die opening 31. As the mandrel descends it becomes coated with the solution in the reservoir and extends into the atmosphere farther and farther, becoming finally substantially entirely coated.

The coated mandrel is then permitted to dry to an adequate extent. The empty reservoir is removed and replaced by another having secured therein a die with a slightly larger aperture 31; the mandrel with the dried tubing material is again placed in the position of FIG. 1; and the reservoir is again sufficiently filled, this time with whatever tubing material is desired for the second layer. The once-coated mandrel is then lowered again through the larger die opening and so receives a second coat of tubing solution on top of the first. This too is permitted to dry to an adequate extent. This proceeding is repeated a number of times, depending upon the number of layers desired in the finished product.

When sufficient coats have been so deposited on the mandrel and have dried to a substantially solid flexible form, the resulting tube is stripped off of the rod. This leaves the mandrel available for a repetition of the just-completed operation. The tubing stripped off of the mandrel is found to be quite smooth and continuous, especially on the inside. The various layers form different zones of the tubing homogeneously joined together. Depending on how they have been treated, they are either quite solid in themselves or are inclusive of a number of small voids to make them somewhat less massive and heavy. The tubing so produced is effective for use in heart surgery and to serve as sections of blood vessels.

If the tubing layers or some of them are to have voids or to be somewhat porous, then a soluble salt or other additive can be incorporated in the initial tubing material, the salt additive, of course, being insoluble in the mixture of the tubing material itself. The additive is later dissolved leaving small voids. It is also possible to employ variations to change the density, color, composition, loading, hydrophobicity and surface energy to give a composite tubing having a wide range of desirable properties.

Sometimes it is desired to treat the mandrel 18 initially to produce an even finer finish on the interior surface of the resulting tube. In this case, the mandrel or rod may first be coated with a thin layer of a curable silicone elastomer so as to provide a glass-like finish on the mandrel which, in turn, provides a glass-like surface in the formation of the interior, blood-contacting layer of the tubing. On the other hand, if rough surfaces are to be provided, then the rod or mandrel may initially be coated with grains of salt (NaCl), which later can be removed from the interior of the tubing to leave corresponding rough pores.

While the lateral freedom of both the mandrel and the die assembly, together with the flow of tubing solution, maintain the mandrel concentric with the die opening 31, it has been found that the same effect can be accomplished with only one of the two elements, for instance the die assembly, laterally restrained. Moreover, it has been found that the mandrel may be held vertically stationary and the die assembly moved upwardly about the mandrel.

The apparatus and method described hereinabove is for a step-by-step operation. If it is desired to make the operation more clearly continuous, then the rod or mandrel can be held as a freely hanging axially stationary pendulum. Since it hangs freely it will, as in the previously described embodiment, still be self-centered in the reservoir opening while the liquid material flows therefrom. Depending upon the tubing material selected, the emerging liquid material then carries a solvent that evaporates rather quickly for prompt setting of the emerging material as a tube. After such an emerging tube has set it can itself serve as the mandrel for subsequent coating. Alternatively, it can be overlaid on another mandrel for subsequent operations. Then, through a subsequent, comparable coating step in a larger die bore 31, there can be afforded an exterior layer of tubing material around the first one.

The arrangement in FIG. 3 is for just such a continuous operation. In this instance the die 29 is held in a reservoir tank 36 by means of a set screw 37 much in the manner that the die 29 is held in the reservoir 26 of FIG. 1. The reservoir 36, however, includes a pressure tight cover 38 into which is secured a connector 39 for attachment to a source of tubing material. The connector 39 extends through the cover 38 and has on its other end a filling tube 41. A mandrel 42 is suspended from the cover 38 by means of a flexible line 43. Preferably the mandrel 42 is hollow and has its upper end connected to a flexible tubing 44 which, in turn, is connected to a sizing fluid connector 46 in the top 38. The opposite end of the sizing fluid connector can be coupled to a source of pressurized air or other fluid for use as will be seen hereinafter. The sizing fluid may have other functions such as curing or coagulation of the formed tubing.

In operation of the arrangement shown in FIG. 3 the mandrel 42 is positioned within the die 29, as shown in the drawing and tubing material is placed into the reservoir 36 through the connector 39 and filling tube 41 so as to reach a level such as at 47. The tubing material, being under pressure, exudes through the annular opening between the mandrel 42 and the die 29 so as to form a tube 48 about the lower end of the mandrel 42. As more and more tubing material is exuded through the annular opening the tube 48 is urged downward on the mandrel 42 and for this purpose the mandrel is preferably tapered throughout that portion of its length extending below the die 29. This taper assists in the movement of the tube as it is being set. Moreover, the mandrel, being hollow and connected to a source of sizing fluid through the connector 56, serves as a passage for the sizing fluid therethrough out an opening 49. Thus, the sizing fluid is emitted into the hollow of the finished tubing 48 and, if the end of the tube 48 is maintained closed, the pressure from the sizing fluid will further assist in the removal of the tube from the mandrel. Alternatively, the inside of the reservoir could be independently pressurized such as with a source of nitrogen. The pressurized nitrogen would not only force the tubing material between the die and the mandrel but would also pass through an opening in the upper part of the mandrel to act as the sizing fluid. In any event the tubing when it is emitted from the die is subjected to a curing or coagulating environment.

Multilayer tubes can be made, as before, by using larger dies and repeating the operation with the previously formed tube. In fact, multiple die and reservoirs can be arranged in tandem along or beyond the mandrel 41 it merely being necessary that the tubing is set sufficiently after leaving one die and before entering the following reservoir. In tandem operations it is not necessary that the additional tubing material be placed under pressure but rather a reservoir similar to that shown in FIG. 1 may be utilized. After the wall of the tube has been found sufficiently thick and strong to maintain its shape the previously formed tube may itself serve as the mandrel.

With an arrangement such as has been described, it is clear that simple fabrication of multilayered structures is possible in which each layer is concentric with the others. The properties of the various layers may themselves vary dramatically by using different materials or even by using a single material which has been modified to vary its bulk, surface, or other properties. In this way a composite overall structure may be prepared with the combination of desired features not easily attainable by other methods of fabrication such as dipping and thermoplastic extrusion.

Thus the completed tube may have inner and outer surfaces very different from the bulk material between them and from each other. The overall distensibility or compliance of the tubing may likewise be varied over a wide range by varying the relative thickness of each layer. Moreover, the arrangement permits the use of reinforcement within the walls of the tube. By interrupting the coating process, a spiral fiber wrapping or other type of reinforcement may be applied to the mandrel over the last deposited layer. After application of the reinforcement the coating process may be continued until all layers have been applied. The resulting tube will then contain reinforcement in its wall and such reinforcement may be used to increase burst strength of the tubing or its resistance to kinking. Moreover, the reinforcement may be applied in the form of reinforcing spirals of polymer on the surface of the precoated mandrel.

Apparatus to produce such an arrangement is shown in FIGS. 4 and 5. In this instance there is provided a frame 51 having rigid platforms 52, 53 and 54 attached thereto.

The upper platform 52 carries a motor 56 to which is attached a drum 57 carrying a line 58 which depends through an opening 59 in the platform 52. The line 59 carries a rectangular cross section rod 61 which passes through an opening 62 in the platform 53. At its lower end the rod 61 carries a mandrel 63 which may be held in place in the rod by means of a pin 64.

Disposed on the platform 53 are four rotation limiting bumpers 66 which are secured to the platform 53 by means of screws 67 extending through slots 68 in the bumpers 66.

The platform 54 carries a die assembly 71 which is rotatably held on the platform 54 by any convenient means such as being set in a circular opening on the platform 54 having a bearing surface at the bottom thereof to prevent the die from passing therethrough. The platform 54 also carries a motor 72 and a gear reduction assembly 73 connected thereto, the other end of which is connected to a gear 74. The gear 74 is arranged to mesh with the cooperating gear teeth 76 carried on the die assembly 71 so that upon operation of the motor 72 the die assembly 71 is rotated about its axis. As can be seen in FIG. 5 which is a cross section of the die assembly, the die itself may include notches 77 so that the space between the die and the mandrel 63 is not merely annular but will include outwardly extending ridges.

The bumpers 66 on the platform 53 are arranged sufficiently close to the rod 61 that rotation of the rod is prevented but it is free to move vertically therethrough. Also some slight movement in the horizontal direction is tolerated so that the mandrel 63 may self-align concentrically in the die assembly 71. Thus, the mandrel is permitted to center itself and is still prevented from rotating. By using the notched die such as described hereinabove an integral reinforcing spiral of polymer can be provided on the surface of a precoated mandrel and such reinforcement may be used in lieu of a separate spiral wrapped reinforcing fiber.

It should be seen that in the operation of the apparatus as shown in FIG. 4 the motor 56 controls the linear speed of the mandrel through the die 71 while the motor 72 controls the rotational speed of the die itself. It should be recognized, however, that the motor 56 may well be eliminated and the apparatus of FIG. 4 utilized much in the way as the apparatus of FIG. 3 with the mandrel 63 being held vertically stationary with the sizing fluid being passed therethrough to assist in removal of the continuously formed tubing from the mandrel.

We claim:
1. A method for fabricating multi-layer tubing comprising positioning a rod vertically within and through a reservoir having a plurality of outlet apertures, maintaining said rod and reservoir free for lateral movement relative to each other in all directions, passing said rod successively through said plurality of outlet apertures in said reservoir, said reservoir containing liquid material for coating said rod and each of said outlet apertures being of successively larger cross-sectional area, permitting said liquid material to solidify on said rod, and separating said rod and said solidified material.

2. A method for fabricating multi-layer tubing comprising positioning a rod vertically within and through a reservoir having successively larger outlet apertures and containing liquid material effective to coat said rod and to dry to a substantial solid, maintaining said rod and reservoir free for lateral movement relative to each other in all directions, passing said rod successively through said successively larger outlet apertures in said reservoir, then drying each layer of said material coating said rod, and then separating said dried layers of coating material from said rod.

3. A method for fabricating multi-layer tubing comprising pendulously supporting a reservoir having an opening in the bottom thereof and containing liquid coating material, pendulously supporting a rod extending through said material and said opening, moving said rod relative to said reservoir and through said opening while said material deposits on said rod, exposing said material so deposited on said rod to a drying medium until said exposed material is substantially dry, enlarging said opening, again moving said rod with dried deposited material thereon through said reservoir and said enlarged opening while further material deposits on said dried deposited material, again exposing material so deposited to a drying medium until said further material is substantially dry, and then removing all of said dried deposited material from said rod.

4. A method for fabricating tubing comprising positioning an elongated mandrel vertically within and through a reservoir having an opening in the bottom thereof and forming an annular opening therebetween, maintaining said mandrel and reservoir free for lateral movement relative to each other in all directions, placing a tubing material in said reservoir and permitting said tubing material to pass through said annular opening to form said tubing.

5. A method as in claim 4 together with the step of providing relative axial movement between said mandrel and said reservoir as said material is permitted to pass through said annular opening.

6. A method as defined in claim 4 together with the step of providing relative rotation between said mandrel and said reservoir about their common axis as said tubing material is permitted to pass through said annular opening.

7. A method as in claim 4 together with the step of restraining said mandrel from axial movement relative to said reservoir and applying pressure to said tubing material to force it through said annular opening.

8. A method as defined in claim 7 together with the step of applying a sizing fluid to the inside of said tubing to assist the removal of said tubing from said mandrel.

9. A method as defined in claim 7 together with the step of applying a sizing and solidifying fluid to the inside of said tubing to assist the removal of said tubing from said mandrel and the solidifying thereof.

10. Apparatus for fabricating tubing comprising a support, a reservoir for tubing solution mounted on said support, said reservoir having an opening in the bottom thereof, a die mounted on said reservoir in said opening, a mandrel, and means for mounting said mandrel on said support substantially in alignment with the vertical axis of said die, said die and said mandrel being free for lateral movement relative to each other in all directions.

11. Apparatus as defined in claim 10 wherein said die and said mandrel are both free for lateral movement relative to said support.

12. Apparatus as defined in claim 10 together with means for restraining lateral movement of said die relative to said support and wherein said mandrel is free for lateral movement relative to said support.

13. Apparatus as defined in claim 10 together with means for restraining lateral movement of said mandrel relative to said support and wherein said die is free for lateral movement relative to said support.

14. Apparatus as in claim 10 together with means for providing relative axial movement between said die and said mandrel.

15. Apparatus as in claim 10 together with means for retaining said mandrel in a fixed axial position with respect to said die, the bottom of said mandrel extending below the bottom of said die.

16. Apparatus as in claim 15 wherein said mandrel is hollow, and includes an opening through its wall at a position below said die, and means for placing sizing fluid on the interior of said mandrel for emission from said opening.

17. Apparatus as defined in claim 10 together with means for providing relative rotation between said die and said mandrel about their common vertical axis.

18. Apparatus as defined in claim 17 wherein said die includes a notch in the periphery of its opening.

* * * * *